(12) United States Patent
Sundick et al.

(10) Patent No.: US 6,737,522 B2
(45) Date of Patent: *May 18, 2004

(54) CHICKEN INTERLEUKIN-15 AND USES THEREOF

(75) Inventors: Roy S. Sundick, Farmington Hills, MI (US); Lily A. Jones, Grosse Point Park, MI (US); David I. Smith, Rochester, MN (US)

(73) Assignee: Wayne State University, Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/907,539

(22) Filed: Jul. 17, 2001

(65) Prior Publication Data

US 2002/0150554 A1 Oct. 17, 2002

Related U.S. Application Data

(62) Division of application No. 09/368,613, filed on Aug. 4, 1999, now Pat. No. 6,287,554, and a division of application No. 08/729,004, filed on Oct. 10, 1996, now Pat. No. 6,190,901.
(60) Provisional application No. 60/005,682, filed on Oct. 17, 1995.

(51) Int. Cl.[7] .................... C07H 21/04; C12N 15/00; C12N 15/63
(52) U.S. Cl. ............... 536/23.51; 536/23.1; 435/320.1
(58) Field of Search ........................ 536/23.11, 23.51; 435/320.11, 455.1, 471

(56) References Cited

U.S. PATENT DOCUMENTS

| | | | |
|---|---|---|---|
| 4,490,289 A | 12/1984 | Stern | |
| 4,992,367 A | 2/1991 | Cullen | |
| 5,106,617 A | 4/1992 | Federicksen et al. | |
| 5,149,788 A | 9/1992 | Bailon et al. | |
| 5,162,503 A | 11/1992 | Bailon et al. | |
| 5,455,337 A | 10/1995 | Devos et al. | |
| 5,536,657 A | 7/1996 | Chua et al. | |
| 5,597,901 A | 1/1997 | Stern | |

FOREIGN PATENT DOCUMENTS

| | | | |
|---|---|---|---|
| EP | 0 293 180 | 11/1988 | ........... C12P/21/02 |
| EP | 0 473 696 B1 | 7/1995 | |
| WO | WO95/27722 | 10/1995 | |
| WO | WO96/04306 | 2/1996 | |
| WO | WO96/37223 | 2/1996 | |
| ZA | 9 402 636 | 11/1994 | |

OTHER PUBLICATIONS

IL–15 Stimulates The Expansion of Aids Virus–specific CTL[1] (The Journal of Immunology, 1996, 157: 3681–3687.
Studies Evaluating The Antitumor Activity And Toxicity of Interleukin–15, a New T Cell Growth Factor: Comparison With Interleukin–2 (Immunex Research And Development Corporation, Seattle, Washington 98101 And Oncology And Immunology Research Section, Lederle Laboratories, Pearl River, New York 10965, 1965.
Dialog(R)File 149:iac(sm) Health & Wellness Db(sm) (C) 1997 Info Access Co. (Il–15 Boosts Systemic Immunity Against B7–1 Gene Transfected Breast Cancer Cells (Interleukin 15).
Lillehoj et al., "Avian Interferon and Interleukin–2. A Review by Comparison With Mammalian Homologues" *Poultry Science Research*, vol. 4, No. 2, pp. 67–85, 1992.
Interleukin–15, A New T Cell Growth Factor: Comparison with Interleukin–2 (Immunex Research and Development Corporation, Seattle, Washington 98101 and Oncology and Immunology Research Section, Lederle Laboratories, Pearl River, New York 10965) 1995.
Sin et al., J. Virol. vol. 73, 501–509, 1999.
Rodolfo and Colombo, Methods, vol. 19, 114–120, 1999.
Openshaw and Hussell, Dev. Biol. Stand., vol. 92, 179–185, 1998.
Armitage et al., "IL–15 Has Stimulatory Activity for the Induction of B Cell Proliferation and Differentiation" Journal of Immunology, vol. 154, No. 2, pp. 483–490, 1995.
Gini et al., "IL–15 A Novel T Cell Growth Factor That Shares Activities and Receptor Components With IL–2" Journal of Leukocyte Biology, vol. 57, No. 5, pp. 763–766, 1995.
Staeheli et al., "Cytokines of Birds: Conserved Functions–A Largely Different Look" Journal of Interferon and Cytokine, vol. 21, No. 12, pp. 993–1010, 2001.

*Primary Examiner*—David Guzo
*Assistant Examiner*—Quang Nguyen
(74) *Attorney, Agent, or Firm*—Darby & Darby

(57) ABSTRACT

The present invention pertains to isolated DNA encoding avian interleukin-15 and to purified interleukin-15 polypeptides.

27 Claims, 3 Drawing Sheets

FIG. 1A

T7 end of the pCDNA1 vector:

5'-TGCTTGGTACCGAGCTCGGATCCACTAGTAACGCCCCCAGTGTGCTCTAAAG-

Noncoding Segment of cDNA: *CAGATAACTGGGACACTGCC

Coding Region of First Open Region Frame (IL-15):

ATGATGTGCAAAGTACTGATCTTTGGCTGTATTTCGGTAGCAACGCTAATG
ACTACAGCTTATGGAGCATCTCTATCATCAGCAAAAAGGAAACCTCTTCAA
ACATTAATAAAGGATTAGAAATATCAAGAACAAGATTCAT
CTCGAGCTCTACACACCAACTGAGACCCAGGAGTGCACCCAGCAAACTCTG
CAGTGTTACCTGGGAGAAGTGGTTACTCTGAAGAAGAAACTGAAGATGAC
ACTGAAATTAAAGAAGAATTTGTAACTGCTATTCAAAATATCGAAAAGAAC
CTCAAGAGTCTTACGGGTCTAAATCACACCGGAAGTGAATGCAAGATCTGT
GAAGCTAACAACAAGAAAAAATTCCTGATTTTCTCCATGAACTGACCAAC
TTTGTGAGATATCTGCAAAAA

FIG. 1B

Sequence of Remaining Insert cDNA:

TAAGCAACTAATCATTTTATTTACTGCTATGTTATTTATTTAATTATTT
AATTACAGATAATTTATATATTTTATCCCGTGGCTAACTAATCTGCTGTCC
ATTCTGGGACCACTGTATGCTCTTAGTCTCGGGTGATATGACGTCTGTTCTA
AGATCATATATTTGATCCTTTCTGTAACCTACGGGCTCAAAATGTACGTTGGA
AAACTGATTGATTCTCACTTTGTCGGTAAAGTGATATGTGTTACTGAAAG
AATTTTTAAAAGTCACTTCTAGATGACATTTAATAAATTTCAG#

Sp6 end of the pcDNA1 vector:

CTTTAGAGCACACTGGGCCCNTCGAGCATGCATCTAGAGGGCC-3'

\* beginning of cDNA

\# end of cDNA

FIG. 2 chicken IL-15 precursor, 143 amino acids

MMCKVLIFGCISVATLMTTAYGASLSSAKRKPLQTLIKDLEILENIKNKI
HLELYTPTETQECTQQTLQCYLGEVVTLKKETEDDTEIKEEFVTAIQNIE
KNLKSLTGLNHTGSECKICEANNKKFPDFLHELTNFVRYLQK

CHICKEN INTERLEUKIN-15 AND USES THEREOF

This is a divisional of U.S. patent application Ser. No. 09/368,613 filed Aug. 4, 1999, which issued as U.S. Pat. No. 6,287,554 and is a divisional of U.S. patent application Ser. No. 08/729,004, filed on Oct. 10, 1996 and now issued as U.S. Pat. No. 6,190,901. U.S. patent application Ser. No. 08/729,004 claims priority to U.S. provisional patent application Serial No. 60/005,682 filed on Oct. 17, 1995. Each of these prior applications is hereby incorporated herein by reference, in its entirety.

FIELD OF INVENTION

The present invention pertains to isolated genes encoding avian interleukin-15 and to purified interleukin-15 polypeptides.

BACKGROUND OF THE INVENTION

Most chickens produced in developed countries for consumption and egg-laying (at least 10 billion per year) are vaccinated to protect them against Marek's disease. All of the egg-laying chickens and breeder stocks are also vaccinated with Newcastle Disease Virus, Infectious Bursal Disease Virus, Infectious Bronchitis Virus, Fowlpox Virus and Coccidial vaccines. For optimal protection, Marek's vaccination is performed either at or before hatching. One obstacle to the development of efficacious pre-hatching and at-hatching vaccination regimens is that the embryonic and newly hatched avian immune system is not fully developed and cannot mount as effective an immune response to the immunogen as at 2–3 weeks after hatching. Thus, there is a need in the art for agents and compositions that enhance the effectiveness of pre- and post-hatching avian vaccines.

Interleukin-2 and interleukin-15 are related cytokines that stimulate the activity and proliferation of T cells in mammals. Though IL-2 and IL-15 both interact with the β and γ chains of the IL-2 receptor, and may share some elements of tertiary structure, the two polypeptides are not homologous and represent distinct gene products.

The genes encoding IL-15 from several different mammalian species share a high degree of homology. For example, human and simian IL-15 share 97% amino acid homology. By contrast, chicken IL-15, which is the subject of the present invention, shares only 25% amino acid identity with mammalian IL-15. Another distinguishing characteristic of chicken IL-15 is that it (and not the mammalian forms) is produced by mitogen-activated spleen cells. Accordingly, the discovery of chicken IL-15 and the finding that it possesses T cell-stimulatory activity provide a novel reagent for vaccine augmentation in avian species. Without wishing to be bound by theory, the bioactivity of mammalian IL-15 in stimulating skeletal muscle development suggests that avian IL-15s are also useful in stimulating growth in avian species.

SUMMARY OF THE INVENTION

The present invention provides isolated and purified DNA encoding avian interleukin-15 (IL-15), as well as cloning and expression vectors comprising IL-15 DNA and cells transformed with IL-15-encoding vectors. Avian species from which IL-15 may be derived include without limitation chicken, turkey, duck, goose, quail and pheasant.

The invention also provides isolated and purified avian IL-15 polypeptide, the native secreted or mature form of which has a molecular mass of about 14 kDa, an isoelectric point of about 6.57, a net charge of −2, and a hydrophilicity index of 0.278, and which has the ability to stimulate mitogen-activated avian T cells and to promote the growth of other cell types. IL-15 according to the present invention may be obtained from native or recombinant sources.

Also encompassed by the invention are sequence-conservative and function-conservative variants of avian IL-15 DNA and IL-15 polypeptides, including, for example, a bioactive IL-15 sequence or sub-fragment that is fused in-frame to a purification sequence.

In another aspect, the invention provides a method for enhancing an immune response in fowl to an immunogen, which is achieved by administering the immunogen before, after, or substantially simultaneously with avian IL-15 in an amount effective to enhance the immune response.

In yet another aspect, the invention provides a vaccine for inducing an immune response in fowl to an immunogen, comprising the immunogen and an effective amount of avian interleukin-15 for immune response enhancement. The immunogen may be derived, for example, from avian pathogens such as Marek's Disease Virus, Newcastle Disease Virus, Infectious Bursal Disease Virus, Infectious Bronchitis Virus, and the like.

BRIEF DESCRIPTION OF THE DRAWINGS

FIG. 1 is an illustration of an 845 nt sequence including 747 nt of cDNA sequence encoding chicken interleukin-15 (IL-15) SEQ ID NO:1.

FIG. 2 is an illustration of a 143-amino acid sequence corresponding to the chicken interleukin-15 precursor polypeptide (SEQ ID NO:2).

DETAILED DESCRIPTION OF THE INVENTION

All patent applications, patents, and literature references cited in this specification are hereby incorporated by reference in their entirety. In case of conflict, the present description, including definitions, will control.

The present invention encompasses interleukin-15 (IL-15) from avian species. The invention provides isolated and purified nucleic acids encoding avian IL-15, as well as IL-15 polypeptides purified from either native or recombinant sources. Avian IL-15 produced according to the present invention may be used in commercial fowl cultivation to promote growth and to enhance the efficacy of avian vaccines.

Nucleic Acids, Vectors, Transformants

The sequence of the cDNA encoding chicken IL-15 is shown in FIG. 1 (SEQ ID NO:1), and the predicted amino acid sequence of chicken IL-15 is shown in FIG. 2 (SEQ ID NO:2). The designation of this avian polypeptide as IL-15 is based on partial amino acid sequence homology to mammalian IL-15 and the ability of the polypeptide to stimulate mitogen-activated T cells (see below). Furthermore, without wishing to be bound by theory, it is predicted that avian IL-15 polypeptides also exhibit one or more of the following bioactivities: activation of NK (natural killer) cells, stimulation of B-Cell maturation, proliferation of mast cells, and interaction with the beta and gamma subunits of the IL-2 receptor.

Because of the degeneracy of the genetic code (i.e., multiple codons encode certain amino acids), DNA sequences other than that shown in FIG. 1 can also encode the chicken IL-15 amino acid sequences shown in FIG. 2.

Such other DNAs include those containing "sequence-conservative" variations in which a change in one or more nucleotides in a given codon results in no alteration in the amino acid encoded at that position. Furthermore, a given amino acid residue in a polypeptide can often be changed without altering the overall conformation and function of the native polypeptide. Such "function-conservative" variants include, but are not limited to, replacement of an amino acid with one having similar physico-chemical properties, such as, for example, acidic, basic, hydrophobic, and the like (e.g., replacement of lysine with arginine, aspartate with glutamate, or glycine with alanine). In addition, amino acid sequences may be added or deleted without destroying the bioactivity of the molecule. For example, additional amino acid sequences may be added at either amino- or carboxy-terminal ends to serve as purification tags, (i.e., to allow one-step purification of the protein, after which they may be chemically or enzymatically removed). Alternatively, the additional sequences may confer an additional cell-surface binding site or otherwise alter the target cell specificity of IL-15.

The chicken IL-15 cDNAs within the scope of the present invention are those of FIG. 1, sequence-conservative variant DNAs, DNA sequences encoding function-conservative variant polypeptides, and combinations thereof. The invention encompasses fragments of avian interleukin-15 that exhibit a useful degree of bioactivity, either alone or in combination with other sequences or components. As explained below, it is well within the ordinary skill in the art to predictively manipulate the sequence of IL-15 and establish whether a given avian IL-15 variant possesses an appropriate stability and bioactivity for a given application. This can be achieved by expressing and purifying the variant IL-15 polypeptide in a recombinant system and assaying its T-cell stimulatory activity and/or growth-promoting activity in cell culture and in animals, followed by testing in the application.

The present invention also encompasses IL-15 DNAs (and polypeptides) derived from other avian species, including without limitation ducks, turkeys, pheasants, quail and geese. Avian IL-15 homologues of the chicken sequence shown in FIG. 1 are easily identified by screening cDNA or genomic libraries to identify clones that hybridize to probes comprising all or part of the sequence of FIG. 1. Alternatively, expression libraries may be screened using antibodies that recognize chicken IL-15. Without wishing to be bound by theory, it is anticipated that IL-15 genes from other avian species will share at least about 70% homology with the chicken IL-15 gene. Also within the scope of the invention are DNAs that encode chicken homologues of IL-15, defined as DNA encoding polypeptides that share at least about 25% amino acid identity with chicken IL-15.

Generally, nucleic acid manipulations according to the present invention use methods that are well known in the art, such as those as disclosed in, for example, *Molecular Cloning, A Laboratory Manual* (2nd Ed., Sambrook, Fritsch and Maniatis, Cold Spring Harbor), or *Current Protocols in Molecular Biology* (Eds. Aufubel, Brent, Kingston, More, Feidman, Smith and Stuhl, Greene Publ. Assoc., Wiley-Interscience, NY, N.Y., 1992).

The present invention encompasses cDNA and RNA sequences and sense and antisense sequences. The invention also encompasses genomic avian IL-15 polypeptide DNA sequences and flanking sequences, including, but not limited to, regulatory sequences. Nucleic acid sequences encoding avian IL-15 polypeptide(s) may also be associated with heterologous sequences, including promoters, enhancers, response elements, signal sequences, polyadenylation sequences, introns, 5'- and 3'- noncoding regions, and the like. Transcriptional regulatory elements that may be operably linked to avian IL-15 polypeptide DNA sequence(s) include without limitation those that have the ability to direct the expression of genes derived from prokaryotic cells, eukaryotic cells, viruses of prokaryotic cells, viruses of eukaryotic cells, and any combination thereof. Other useful heterologous sequences are known to those skilled in the art.

The nucleic acids of the present invention can be modified by methods known to those skilled in the art to alter their stability, solubility, binding affinity, and specificity. For example, the sequences can be selectively methylated. The nucleic acid sequences of the present invention may also be modified with a label capable of providing a detectable signal, either directly or indirectly. Exemplary labels include radioisotopes, fluorescent molecules, biotin, and the like.

The present invention also provides vectors that include nucleic acids encoding the avian IL-15 polypeptide(s). Such vectors include, for example, plasmid vectors for expression in a variety of eukaryotic and prokaryotic hosts. Preferably, vectors also include a promoter operably linked to the avian IL-15 polypeptide encoding portion. The encoded avian IL-15 polypeptide(s) may be expressed by using any suitable vectors and host cells as explained herein or otherwise known to those skilled in the art.

Vectors will often include one or more replication systems for cloning or expression, one or more markers for selection in the host such as, for example, antibiotic resistance, and one or more expression cassettes. The inserted coding sequences may be synthesized, isolated from natural sources, prepared as hybrids, or the like. Ligation of the coding sequences to the transcriptional regulatory sequences may be achieved by methods known to those skilled in the art. Suitable host cells may be transformed/transfected/infected by any suitable method including electroporation, $CaCl_2$- or liposome-mediated DNA uptake, fungal infection, microinjection, microprojectile, or the like.

Suitable vectors for use in practicing the present invention include without limitation YEp352, pcDNAI (In Vitrogen, San Diego, Calif.), pRc/CMV (InVitrogen), and pSFV1 (GIBCO/BRL, Gaithersburg, Md.). One preferred vector for use in the invention is pSFV1. Suitable host cells include *E. Coli*, yeast, COS cells, PC12 cells, CHO cells, GH4C1 cells, BHK-21 cells, and amphibian melanophore cells. BHK-21 cells are a preferred host cell line for use in practicing the present invention.

Nucleic acids encoding avian IL-15 polypeptide(s) may also be introduced into cells by recombination events. For example, such a sequence can be microinjected into a cell, effecting homologous recombination at the site of an endogenous gene encoding the polypeptide, an analog or pseudogene thereof, or a sequence with substantial identity to an avian IL-15 polypeptide-encoding gene. Other recombination-based methods such as non-homologous recombinations, and deletion of endogenous gene by homologous recombination, especially in pluripotent cells, may also be used.

IL-15 Polypeptides

The chicken IL-15 gene (the cDNA of which is shown in FIG. 1) encodes a polypeptide of 143 amino acids (FIG. 2). Without wishing to be bound by theory, by comparison with simian IL-15, and by use of an accepted procedure to predict signal peptidase cleavage sites (Von Heijne, *Nuc.Acids Res.*, 14:4683, 1986), it is predicted that an aminoterminal leader sequence of about 22 amino acids (secretion signal peptide)

is cleaved from the primary translation product to produce mature IL-15. The predicted mature sequence of 121 amino acids is further characterized by a predicted molecular weight of 13,971 daltons; an isoelectric point of 6.57; four cysteine residues (at amino acids numbers 63, 70, 116, and 119 in the precursor IL-15 shown in FIG. 2) that correspond to four cysteines conserved among human, mouse, and monkey IL-15 and that are believed to participate in intramolecular disulfide bonding; and one consensus site for N-linked glycosylation (at asparagine 110 of the sequence shown in FIG. 2) which corresponds to a similar site in human IL-15.

Purification of IL-15 from natural or recombinant sources may be achieved by methods well-known in the art, including without limitation ion-exchange chromatography, reverse-phase chromatography on C4 columns, gel filtration, isoelectric focusing, affinity chromatography, immunoaffinity chromatography, and the like. In a preferred embodiment, large quantities of bioactive IL-15 may be obtained by constructing a recombinant DNA sequence comprising the coding region for IL-15 fused in frame to a sequence encoding 6 C-terminal histidine residues in the pSFV1 replicon (GIBCO/BRL). mRNA encoded by this plasmid is synthesized using techniques well-known to those skilled in the art and introduced into BHK-21 cells by electroporation. The cells synthesize and secrete mature glycosylated IL-15 polypeptides containing 6 C-terminal histidines. The modified IL-15 polypeptides are easily purified from the cell supernatant by affinity chromatography using a histidine-binding resin (His-bind, Novagen, Madison, Wis.).

Avian IL-15 polypeptides isolated from any source can be modified by methods known in the art. For example, avian IL-15 may be phosphorylated or dephosphorylated, glycosylated or deglycosylated, and the like. Especially useful are modifications that alter avian IL-15 solubility, stability, and binding specificity and affinity.

Anti-IL-15 Antibodies

The present invention encompasses antibodies that are specific for avian IL-15 polypeptides identified as described above. The antibodies may be polyclonal or monoclonal, and may discriminate avian IL-15s from different species, identify functional domains, and the like. Such antibodies are conveniently made using the methods and compositions disclosed in Harlow and Lane, *Antibodies, A Laboratory Manual*, Cold Spring Harbor Laboratory, 1988, other references cited herein, as well as immunological and hybridoma technologies known to those in the art. Where natural or synthetic avian IL-15-derived peptides are used to induce an avian IL-15-specific immune response, the peptides may be conveniently coupled to a suitable carrier such as KLH and administered in a suitable adjuvant such as Freund's. Preferably, selected peptides are coupled to a lysine core carrier substantially according to the methods of Tam (1988) *Proc. Natl. Acad. Sci. USA*, 85:5409–5413. The resulting antibodies may be modified to a monovalent form e.g. Fab, FAB', or FV. Anti-idiotypic antibodies, especially internal imaging anti-idiotypic antibodies, may also be prepared using known methods.

In one embodiment, purified avian IL-15 is used to immunize mice, after which their spleens are removed, and splenocytes used to form cell hybrids with myeloma cells to obtain clones of antibody-secreting cells according to techniques that are standard in the art. The resulting monoclonal antibodies secreted by such cells are screened using in vitro assays for the following activities: binding to avian IL-15, inhibiting the receptor-binding activity of IL-15, and inhibiting the T-cell stimulatory activity of IL-15.

Anti-avian IL-15 antibodies may be used to identify and quantify avian IL-15, using immunoassays such as ELISA, RIA, and the like. Anti-avian IL-15 antibodies may also be used to immunodeplete extracts of avian IL-15. In addition, these antibodies can be used to identify, isolate, and purify avian IL-15s from different sources, and to perform subcellular and histochemical localization studies.

Applications

Avian IL-15 produced according to the present invention can be used beneficially in homologous or heterologous avian species, for example, to stimulate activated T-cells (Grabstein et al., *Science*, 264:965, 1994) and B-cells (Armitage et al., *J. Immunol.*, 154:483, 1995) and/or to promote the growth of non-immune cells, such as, for example, muscle cells (Quinn et al., *Endocrinol.* 136:3669, 1995).

Vaccines

The present invention encompasses methods and compositions for enhancing the efficacy of an immune response in avian species. In this embodiment, avian IL-15 is used in conjunction with an immunogen for which it is desired to elicit an immune response. For example, in avian vaccines, such as those against Marek's disease, Newcastle Disease Virus, and other pathogens such as Infectious Bursal Disease Virus and Infectious Bronchitis Virus, it is desirable to include avian IL-15 in the vaccine to enhance the magnitude and quality of the immune response. For this purpose, IL-15 purified from native or recombinant sources as described above is included in the vaccine formulation at a concentration ranging from about 0.01 $\mu$g to about 1.0 $\mu$g per vaccine per chicken.

IL-15 may be administered in conjunction with a live (i.e., replicating) vaccine or a non-replicating vaccine. Non-limiting examples of replicating vaccines are those comprising native or recombinant viruses or bacteria, such as modified turkey herpesvirus or modified fowlpox virus. Non-limiting examples of non-replicating vaccines are those comprising killed or inactivated viruses or other microorganisms, or crude or purified antigens derived from native, recombinant, or synthetic sources, such as, for example, coccidial vaccines. Commercial sources for avian vaccines include without limitation: Rhone Merieux Laboratoire-IFFA (Lyon, France); Intervet International BV (Boxmeer, The Netherlands); Mallinckrodt Veterinary; Solvay Animal Health (Mendota Heights, Minn.); Hoechst-Roussel (Knoxville, Tenn.); and Nippon Zeon Co., Ltd. (Kawasaki-Kiu, Japan).

In one embodiment, the gene encoding IL-15 is incorporated into a recombinant virus, which is then formulated into a live vaccine. The IL-15 gene is incorporated into the virus so that its expression is controlled by an appropriate promoter. Administration of the vaccine results in the expression of bioactive IL-15 in close temporal and spatial proximity to the desired immune response, thus enhancing the vaccine's efficacy.

IL-15 may be administered to birds as part of a vaccine formulation either before or after hatching, preferably before hatching, using methods known in the art such as those described in U.S. Pat. Nos. 5,034,513 and 5,028,421.

Growth Promotion

The present invention provides methods and compositions for enhancing the growth of avian species for medical and/or commercial purposes. In this embodiment, IL-15 is administered to birds using any appropriate mode of administration. For growth promotion, IL-15 is administered in amounts ranging from about 0.25 $\mu$g/kg/day to about 25 $\mu$g/kg/day. It will be understood that the required amount of IL-15 can be determined by routine experimentation well-known in the art, such as by establishing a matrix of dosages and frequencies and comparing a group of experimental units or subjects to each point in the matrix.

According to the present invention, native or recombinant avian IL-15 may be formulated with a physiologically acceptable carrier, such as, for example, phosphate buffered saline or deionized water. The formulation may also contain excipients, including lubricant(s), plasticizer(s), colorant(s), absorption enhancer(s), bactericide(s), and the like that are well-known in the art. The IL-15 polypeptide of the invention may be administered by any effective means, including without limitation intravenous, subcutaneous, intramuscular, transmucosal, topical, or oral routes. For subcutaneous administration, for example, the dosage form may consist of IL-15 in sterile physiological saline. For oral administration, IL-15, with or without excipients, may be micro- or macro-encapsulated in, e.g., liposomes and microspheres. Dermal patches (or other slow-release dosage forms) may also be used.

The following examples are intended to further illustrate the invention without limiting its scope thereof.

EXAMPLE 1

Cloning of the Chicken IL-15 Gene

To clone chicken IL-15, a chicken spleen cell cDNA library derived from spleen cells that had been activated with concanavalin A was utilized (Kaplan, *J. Immunol*, 151:628, 1993). 5000 colonies were grown overnight at 35° C. on LB agar plates containing 30 μg/ml ampicillin and 10 μg/ml tetracycline. 15–20 colonies were pooled and transferred to 10 ml Terrific Broth (containing the same antibiotics) and grown overnight. Plasmid DNA from each pool was then isolated by published procedures (Maniatis, Section 1.28), treated with RNAase (10 μg/ml), and stored in TE buffer.

The plasmid DNAs were transfected into COS-7(ATCC) cells using Lipofectamine (GIBCO/BRL, Gaithersburg, Md.). 1 μg of each plasmid pool was mixed with 3 μl Lipofectamine in 100 μl Opti-MEM medium (GIBCO/BRL), incubated for 30 min, and then placed on COS-7 cells that had been grown to 80–90% confluence in 12-well plates and rinsed in serum-free medium. The cells and DNA were incubated for 5 hrs at 37° C. with Dulbecco's MEM in the absence of serum and antibiotics, and then supplemented with the same medium containing 10% fetal calf serum and incubated overnight at 37° C. The next day, the medium was replaced with Dulbecco's MEM containing 10% fetal calf serum, penicillin, and streptomycin. After an additional 24 hrs of incubation, the medium was collected and stored at −20° C.

The cell supernatants were tested for IL-15 activity as described in Example 2 below. Five pools with the highest stimulation indices (1.6 to 2.1) exhibited levels of activity that were greater than 2 standard deviations from the mean of the remaining 278 pools. Three of the five pools remained positive in a second screen, and were subdivided into pools of 6. Plasmid DNA extracted from the secondary pools was used to transfect COS-7 cells and the supernatants were tested for IL-2-like activity. As described below in Example 2, three positive pools were identified and subdivided to yield individual clones; from each pool at least one positive clone was isolated.

The complete cDNA inserts of all three positive clones were sequenced using the automated Applied Biosystems Model 373A sequencing system. The flanking T7 and SP6 primers contained in the pcDNA1 vector were used to prime the sequencing reaction. Two of the clones, B2.16.2 and M2.12.1, were identical and coded for the cDNA sequence shown in FIG. 1. Clone F19.84 was similar to those two clones, but was missing the 20 nt at its 5' end (i.e., starting at the first ATG of the coding region) and contained a poly T tail of at least 100 nt at its 3' end.

The entire 747 nt sequence (FIG. 1, SEQ ID NO:1) was analyzed using a BLAST search (which accesses all of the major international nucleotide data banks). No significant homology was detected with any other known sequence. The sequence was also analyzed using the MacVector software program (MacVector 4.0; International Biotechnologies, Inc., New Haven, Conn.) on a Mac IIci computer. This analysis revealed an open reading frame flanked at its 5' end by a Kozak consensus sequence for translation initiation. The predicted amino acid sequence of this open reading frame is shown in FIG. 2 (Seq ID NO:2). This amino acid sequence was analyzed using a BLASTP search (which accesses all of the major international protein data banks) revealing significant homology with monkey and human precursor IL-15.

The predicted amino acid sequence of chicken IL-15 consists of a 143 amino acid polypeptide having a predicted molecular weight of 16,305 and an isoelectric point of 6.37. Based on the hydrophobicity of its amino terminal end and by comparison with known signal peptide cleavage sites (von Heijne, *Nucleic Acids Res.* 14:4683, 1986) it is predicted that cleavage between glycine-22 and alanine-23 results in the removal of an aminoterminal leader sequence of about 22 amino acids (secretion signal peptide) from the primary product to produce mature IL-15.

The predicted mature IL-15 sequence of 121 amino acids has a predicted molecular weight of 13,971, an isoelectric point of 6.57, and a possible N-linked glycosylation site (at asparagine 110 of FIG. 2). Comparisons between the predicted amino acid sequences of IL-15 from monkey, human, mouse and chicken and analysis of the tertiary structure of monkey IL-15 (Grabstein, *Science*, 264:965, 1994) suggest that four cysteines in chicken IL-15 (positions 63, 70, 116 and 119 of precursor IL-15, FIG. 2) are conserved and form intrachain disulfide bonds.

EXAMPLE 2

Bioactivity Assay for Chicken IL-15

Bioactivity assays for IL-15 are performed as follows: Concanavalin A (ConA)-activated splenic T cells are prepared by incubating chicken spleen cells ($10^7$ cells/ml) with Con A (10 μg/ml) (Sigma Chemical Co., St. Louis, Mo.) in RPMI 1640 medium (Sigma) containing 2 mg/ml BSA, antibiotics and glutamine at 40° C. for 24 hrs. The medium is then replaced with Iscoves' medium (Sigma) containing 2% normal chicken serum (Sigma) and 0.05M alpha-methyl pyrannoside (Sigma) for an additional 2–4 days, diluting the cells in additional medium as needed. Blast cells are purified from this mixture by gently layering them on a Histopaque density gradient (Sigma) and centrifuging them according to the manufacturer's instructions. The cells are then washed three times and finally resuspended in assay medium (Iscoves' containing 2% normal chicken serum (Sigma)).

For the assay, $2 \times 10^4$ blast cells are placed in roundbottom 96 well plates in assay medium containing IL-15 (such as, e.g., dilutions of supernatant from transfected COS-7 cells) or appropriate controls. After overnight incubation at 40° C., the cells are pulsed for 6 hrs with $^3$H-thymidine (0.5 $\mu$Ci) (New England Nuclear, Boston, Mass.)+fluorodeoxyuridine ($10^{-6}$M) (Sigma). The cells are then harvested on glass fiber filters (Whatman, Clifton, N.J.), and the radioactivity is measured in a liquid scintillation counter. IL-15 is expressed as a stimulation index, which is the radioactivity in experimental samples—the radioactivity in controls (non-transfected COS-7 supernatants). A typical result is shown in Table 1.

TABLE 1

| SOURCE OF PLASMID DNA | | Stimulation indices | | | |
|---|---|---|---|---|---|
| DNA | Designation | 1/10 dil[a] | 1/10 dil[b] | 1/33 dil[b] | 1/100 dil[b] |
| PRIMARY POOLS | A19 | 1.6 | 1.9 | 1.3 | 1.2 |
| | B2 | 2.1 | 4.2 | 2.3 | 1.7 |
| | E7 | 1.8 | 1.7 | 1.5 | 0.9 |
| | F19 | 1.8 | 3.5 | 2.0 | 1.2 |
| | M2 | 1.7 | 3.2 | 1.9 | 1.3 |
| | Ave. of 278 ± SD | 1.1 ± 0.1 | | | |
| | Ave. of 3 Neg. pools | | 1.4 | 1.3 | 1.1 |
| SECONDARY POOLS | A19.7 | | 0.7 | 1.9 | |
| | B2.16 | | 6.0 | 3.5 | |
| | F19.8 | | 9.8 | 3.4 | |
| | M2.12 | | 3.2 | 2.2 | |
| INDIVIDUAL CLONES | B2.16.2 | | 6.6 | 3.3 | 2.7 |
| | F19.8.4 | | 7.5 | 4.0 | 3.0 |
| | M2.12.1 | | 7.2 | 3.9 | 3.6 |

[a]First screening at 1/10 dil.
[b]A repeat transfection using 5 positive and 3 negative primary pools

EXAMPLE 3

Expression and Purification of IL-15

To obtain high-level expression of chicken IL-15 in mammalian cells, the pSFV1 eukaryotic expression vector (which includes the Semliki Forest Virus replicon) is used (GIBCO/BRL, Gaithersburg, Md.). Use of this vector allows for signal peptide cleavage, glycosylation, and secretion of mature active protein. In one embodiment, the recombinant vector encodes an additional six histidine residues at the carboxyterminus of the native IL-15 sequence, allowing the efficient single step purification of the secreted protein on a nickel column (Novagen, Madison, Wis.).

Primers were constructed that include 5' and 3' sequences flanking the coding region of IL-15 cDNA. The 3' primer also includes nucleotides coding for 6 histidines. These primers were used in polymerase chain reaction (PCR), using as a template the entire IL-2 cDNA contained within the pcDNA1 plasmid. The resulting amplified cDNA, including the histidine-coding sequences, was ligated into the pSFV1 plasmid (GIBCO/BRL). The plasmid was obtained by transforming DH5 E. coli (GIBCO/BRL) and selecting transformants on agar plates and broth containing ampicillin.

This plasmid is used as a template to produce mRNA in vitro, using manufacturer's protocols. The mRNA is transfected into BHK-21 cells by electroporation, using 10 $\mu$g RNA per $10^7$ cells, after which the cells are incubated for 1–3 days. The cell supernatant is harvested and passed through a resin matrix (His-Bind resin; Novagen, Madison, Wis.) using a suitable buffer system (His-bind buffer kit; Novagen). Up to 20 mg of tagged protein can be purified on a single 2.5 ml column. The IL-15 is eluted from the column with the elution buffer provided in the kit. It is estimated that BHK-21 cells growing in 50 ml medium synthesize about 25 mg total protein, with up to 5% comprising a recombinantly expressed and secreted protein. This corresponds to approximately 1.25 mg of cIL-15.

EXAMPLE 4

Use of Avian IL-15 in Vaccines

The following experiments are performed to evaluate the immune-enhancing activity of chicken IL-15 in chicken vaccines.

Chicken IL-15 cDNA is inserted into two viral vectors (derived from turkey herpesvirus and fowlpox virus, respectively) that are used for the expression of recombinant proteins in chickens (Morgan et al., *Avian Diseases,* 36:858, 1992; Yanagida et al., *J. Virol.,* 66:1402, 1992; Nazerian et al., *J. Virol,* 66:1409, 1992). These IL-15-modified live viral vectors are administered to newly hatched chicks simultaneously with the administration of various vaccines currently available. Six days later the chicks are challenged with the corresponding virulent viruses and observed for 8 weeks for the development of disease. The incidence of disease in these chicks is compared with controls that do not receive the IL-15-modified live viral vectors. A sample protocol (including expected results) is shown in Table 2.

TABLE 2

| Group # | Treatment on day 1 | Challenge at day 6 | % expected with disease |
|---|---|---|---|
| 1 | none | none | 0 |
| 2 | none | virulent Marek's | >80% |
| 3 | HVT (not modified) | virulent Marek's | 20% |
| 4 | HVT-IL-15[a] | virulent Marek's | 0 to 10% |
| 5 | HVT (not modified) + HVT-IL-15 | virulent Marek's | 0 to 10% |
| 6 | none | virulent NDV | >80% |
| 7 | HVT-IF-15 | virulent NDV | 30% to >50% |
| 8 | NDV vaccine | virulent NDV | 20% |
| 9 | NDV vaccine + HVT-IL-15 | virulent NDV | 0 to 10% |

[a]herpesvirus of turkeys expressing IL-15

In an alternative procedure, newly hatched chicks are injected intramuscularly with 100 $\mu$g of a plasmid containing cDNA for chicken IL-15, using the methods described in Ulmer, *J. B. Science,* 259:1745–1749, 1993. These chicks, and control chicks receiving a control vector lacking IL-15 cDNA, are vaccinated on day 2 with chicken vaccines and then challenged on day 7 with the corresponding virulent viruses. They are observed for 8 weeks for signs of disease. It is expected that chicks injected with the pcDNA1 vector containing IL-15 cDNA will exhibit a reduced incidence of disease relative to controls.

Finally, IL-15 protein purified by the procedure described in Example 3 is administered intramuscularly to chicks at hatching, followed by a single daily administration on each of the following four days. Chicks are divided into three groups, receiving 0.01, 0.1 or 1.0 µg per injection per day. A fourth group receives placebo injections. At hatching all chicks are vaccinated with chicken vaccines and then challenged on day 7 with the corresponding virulent viruses. They are then observed for 8 weeks for signs of disease. It is expected that chicks injected with IL-15 will exhibit a reduced incidence of disease relative to controls.

EXAMPLE 5

Use of Avian IL-15 in Growth Promotion

Mammalian IL-15 stimulates muscle growth (Quinn, L. S., *Endocrin.*, 136:3669, 1995) and semi-pure chicken IL-2 stimulates chicken body weight and increases feed conversion (U.S. Pat. No. 5,028,421). To evaluate the growth-promoting activity of avian IL-15, the methods described in Example 4 above may be used to administer IL-15 cDNA in a viral or plasmid vectors recombinant IL15 protein. Experimental and control chicks are monitored for weight gain and feed conversion for a period of six weeks. It is expected that one or more of these protocols will enhance chicken growth over controls.

What is claimed is:

1. An isolated nucleic acid which:
   (a) comprises a nucleic acid sequence having at least 70% sequence homology, determined by a BLAST algorithm, to the sequence set forth in nucleotides 87–449 of SEQ ID NO:1; and
   (b) encodes a polypeptide capable of stimulating thymidine incorporation in mitogen activated avian T-cells.

2. The complement of a nucleic acid according to claim 1.

3. An isolated nucleic acid according to claim 1 or 2, which nucleic acid is an avian nucleic acid isolated from chicken.

4. A vector construct comprising the nucleic acid of claim 1.

5. The vector construct according to claim 4, in which said nucleic acid is operatively associated with a promoter element capable of expressing the nucleic acid in a host cell.

6. The vector construct according to claim 4, in which the construct is a recombinant virus.

7. The vector construct according to claim 6, in which the recombinant virus is a turkey herpes virus or a fowl pox virus.

8. An isolated nucleic acid which:
   (a) hybridizes to the full length of a nucleic acid having the complementary sequence of nucleotides 87–449 in SEQ ID NO:1 under conditions comprising (i) hybridization in 6×SSC and 0.5% SDS, and (ii) washing at 68° C. in 0.1×SSC and 0.5% SDS; and
   (b) encodes a polypeptide capable of stimulating thymidine incorporation in mitogen activated avian T-cells.

9. The complement of a nucleic acid according to claim 8.

10. An isolated nucleic acid according to claim 8 or 9, which nucleic acid is an avian nucleic acid isolated from chicken.

11. An isolated nucleic acid which:
    (a) hybridizes to the full length of a nucleic acid having the complementary sequence of nucleotides 87–449 in SEQ ID NO:1 under conditions comprising (i) hybridization in 6×SSC and 0.5% SDS, and (ii) washing at room temperature in 2×SSC and 0.5% SDS; and
    (b) encodes a polypeptide capable of stimulating thymidine incorporation in mitogen activated avian T-cells.

12. The complement of a nucleic acid according to claim 11.

13. An isolated nucleic acid according to claim 11 or 12, which nucleic acid is an avian nucleic acid isolated from chicken.

14. A vector construct comprising the nucleic acid of claim 8 or 11.

15. A The vector construct according to claim 14, in which said nucleic acid is operatively associated with a promoter element capable of expressing the nucleic acid in a host cell.

16. The vector construct according to claim 14, in which the construct is a recombinant virus.

17. The vector construct according to claim 16, in which the recombinant virus is a turkey herpes virus or a fowl pox virus.

18. An isolated nucleic acid having an open reading frame that encodes a polypeptide comprising the sequence of amino acid residues 23–143 set forth in SEQ ID NO:2 (FIG. 2).

19. The complement of a nucleic acid according to claim 18.

20. An isolated nucleic acid according to claim 18 or 19, which nucleic acid is an avian nucleic acid isolated from chicken.

21. An isolated nucleic acid according to claim 18, wherein the polypeptide comprises the amino acid sequence set forth in SEQ ID NO:2 (FIG. 2).

22. The complement of a nucleic acid according to claim 21.

23. An isolated nucleic acid according to claim 21 or 22 which nucleic acid is an avian nucleic acid isolated from chicken.

24. A vector construct comprising the nucleic acid of claim 18 or 21.

25. The vector construct according to claim 24, in which said nucleic acid is operatively associated with a promoter element capable of expressing the nucleic acid in a host cell.

26. The vector construct according to claim 24, in which the construct is a recombinant virus.

27. The vector construct according to claim 26, in which the recombinant virus is a turkey herpes virus or a fowl pox virus.

* * * * *

SEQUENCE LISTING

<160> NUMBER OF SEQ ID NOS: 2

<210> SEQ ID NO 1
<211> LENGTH: 747
<212> TYPE: DNA
<213> ORGANISM: Gallus domesticus

<400> SEQUENCE: 1

```
cagataactg ggacactgcc atgatgtgca aagtactgat ctttggctgt atttcggtag      60
caacgctaat gactacagct tatggagcat ctctatcatc agcaaaaagg aaacctcttc     120
aaacattaat aaaggattta gaaatattgg aaaatatcaa gaacaagatt catctcgagc     180
tctacacacc aactgagacc caggagtgca cccagcaaac tctgcagtgt tacctgggag     240
aagtggttac tctgaagaaa gaaactgaag atgacactga aattaaagaa gaatttgtaa     300
ctgctattca aaatatcgaa aagaacctca agagtcttac gggtctaaat cacaccggaa     360
gtgaatgcaa gatctgtgaa gctaacaaca agaaaaaatt tcctgatttt ctccatgaac     420
tgaccaactt tgtgagatat ctgcaaaaat aagcaactaa tcatttttat tttactgcta     480
tgttatttat ttaattattt aattacagat aatttatata ttttatcccg tggctaacta     540
atctgctgtc cattctggga ccactgtatg ctcttagtct gggtgatatg acgtctgttc     600
taagatcata tttgatcctt tctgtaacct acgggctcaa aatgtacgtt ggaaaactga     660
ttgattctca ctttgtcggt aaagtgatat gtgtttactg aaagaatttt taaaagtcac     720
ttctagatga catttaataa atttcag                                         747
```

<210> SEQ ID NO 2
<211> LENGTH: 143
<212> TYPE: PRT
<213> ORGANISM: Gallus domesticus

<400> SEQUENCE: 2

```
Met Met Cys Lys Val Leu Ile Phe Gly Cys Ile Ser Val Ala Thr Leu
1               5                   10                  15

Met Thr Thr Ala Tyr Gly Ala Ser Leu Ser Ser Ala Lys Arg Lys Pro
            20                  25                  30

Leu Gln Thr Leu Ile Lys Asp Leu Glu Ile Leu Glu Asn Ile Lys Asn
        35                  40                  45

Lys Ile His Leu Glu Leu Tyr Thr Pro Thr Glu Thr Gln Glu Cys Thr
    50                  55                  60
```

-continued

```
Gln Gln Thr Leu Gln Cys Tyr Leu Gly Glu Val Val Thr Leu Lys Lys
65                  70                  75                  80

Glu Thr Glu Asp Asp Thr Glu Ile Lys Glu Glu Phe Val Thr Ala Ile
                85                  90                  95

Gln Asn Ile Glu Lys Asn Leu Lys Ser Leu Thr Gly Leu Asn His Thr
                100                 105                 110

Gly Ser Glu Cys Lys Ile Cys Glu Ala Asn Asn Lys Lys Lys Phe Pro
            115                 120                 125

Asp Phe Leu His Glu Leu Thr Asn Phe Val Arg Tyr Leu Gln Lys
            130                 135                 140
```